United States Patent [19]
Hossain et al.

[11] Patent Number: 5,841,016
[45] Date of Patent: Nov. 24, 1998

[54] ULTRA-LOW LEVEL STANDARD FOR CONCENTRATION MEASUREMENTS

[75] Inventors: Tim Z. Hossain; John Lowell, both of Austin, Tex.

[73] Assignee: Advanced Micro Devices, Inc., Sunnyvale, Calif.

[21] Appl. No.: 712,715

[22] Filed: Sep. 12, 1996

[51] Int. Cl.⁶ .................................................. G01D 18/00
[52] U.S. Cl. ........................................... 73/1.01; 378/207
[58] Field of Search ........................ 73/1.01; 250/252.1; 378/207

[56] References Cited

U.S. PATENT DOCUMENTS

| | | | |
|---|---|---|---|
| 3,064,130 | 11/1962 | Di Ianni et al. | 250/252.1 |
| 3,107,299 | 10/1963 | Jachter | 250/252.1 |
| 3,519,821 | 7/1970 | Bolster | 250/252.1 |
| 3,751,661 | 8/1973 | Packer et al. | 378/47 |
| 3,859,179 | 1/1975 | Staples | 205/122 |
| 4,092,539 | 5/1978 | Pao et al. | 250/252.1 X |
| 4,119,847 | 10/1978 | Waggoner | 250/252.1 |
| 4,256,960 | 3/1981 | Snider | 250/252.1 |
| 4,270,052 | 5/1981 | King | 250/432 PD |
| 4,406,947 | 9/1983 | Burton et al. | 250/252.1 |
| 4,510,573 | 4/1985 | Boyce et al. | 364/498 |
| 4,524,279 | 6/1985 | Christianson et al. | 250/252.1 X |
| 4,771,177 | 9/1988 | Brown | 250/252.1 X |
| 4,779,621 | 10/1988 | Mattson | 128/654 |

(List continued on next page.)

FOREIGN PATENT DOCUMENTS

| | | | |
|---|---|---|---|
| 59-116533 (A) | 5/1984 | Japan | 378/207 |
| 60-135842 (A) | 7/1985 | Japan | 250/252.1 R |
| 6-148337 (A) | 5/1994 | Japan | 250/252.1 R |
| 1146-091-A | 1/1984 | U.S.S.R. | 378/207 |
| 1469-402-A | 4/1987 | U.S.S.R. | 378/207 |
| 984834 | 3/1965 | United Kingdom | 250/252.1 |

OTHER PUBLICATIONS

Patent Abstracts of Japan Grp P1598, vol. 17, No. 461, Abs. p–6, dated Aug. 23, 1993 (05–107388) Ueda et al. "Method for Measuring Neutron Effective Multiplication Constant During Storage of Radiation Fuel.".

"Automatic Calibration of Radiation Monitoring films" Abstract, UKAEA Res. Group; AERE, Harwell, Berks., England; Report No. AERE–R6037, Mar. 1969.

John Volpe, "Bettis Reactor Engineering School Nuclear Physics Notes", Rev. 1; Topic 8—Radioactivity, pp. 8–1 to 8–8, Aug. 1988.

*Minutes of ISO/TC201/WG2 on Total Reflection X–Ray Fluorescence Spectroscopy*, ISO/TC 201/WG2 N 27, Jan. 29, 1996.

(List continued on next page.)

*Primary Examiner*—Ronald L. Biegel
*Assistant Examiner*—Paul D. Amrozowicz
*Attorney, Agent, or Firm*—Skjerven, Morrill, MacPherson, Franklin & Friel, LLP; David W. O'Brien

[57] ABSTRACT

Concentration measurement equipment is calibrated by performing a concentration measurement on a reference standard sample which includes a radioactive marker element. Because a count of decay products can be correlated with the number of atoms of the radioactive marker element, a precise count of decay products of the radioactive marker element is used to calculate an otherwise unknown number of atoms of the radioactive marker element on the reference standard sample. The calculated number of atoms of radioactive marker element is then used to calibrate a concentration measurement of the radioactive marker element by the concentration measurement device. Suitable radioactive marker elements for use in calibrating concentration measurement equipment include Pm-147 and Tc-99. Materials, methods and systems in accordance with the teachings of the invention are useful for calibrating concentration measurements and measurement equipment, including Total X-ray Fluorescence (TXRF) and Time Of Flight-Secondary Ion Mass Spectroscopy (TOF-SIMS) measurements and measurement equipment.

34 Claims, 3 Drawing Sheets

U.S. PATENT DOCUMENTS

| | | | |
|---|---|---|---|
| 4,912,323 | 3/1990 | Bhat et al. | 250/252.1 |
| 4,985,906 | 1/1991 | Arnold | 378/18 |
| 5,024,801 | 6/1991 | Impink, Jr. et al. | 376/217 |
| 5,164,093 | 11/1992 | Chilton et al. | 210/688 |
| 5,210,778 | 5/1993 | Massart | 378/53 |
| 5,373,544 | 12/1994 | Goebel | 378/71 |
| 5,376,803 | 12/1994 | McFee et al. | 250/252.1 X |
| 5,497,407 | 3/1996 | Komatsu et al. | 378/45 |
| 5,559,324 | 9/1996 | Rapkin et al. | 250/252.1 |
| 5,637,506 | 6/1997 | Goken et al. | 436/57 |

OTHER PUBLICATIONS

*Third Working Draft, Surface Chemical Analysis—Determination Of Contamination Elements Contents On Silicone Wafer—Total Reflections X–Ray Fluorescence Spectroscopy (TXRF)*, ISO/TC 201/WG2 N 26, Nov. 27, 1995.

R. S. Hockett, Proceedings from the Denver X–Ray Conference, *An Update on Standards Activity for TXRF and the Challenges Ahead*, Aug. 1995, pp. 1–4.

R.S. Hockett, *TXRF Detection of Subsurface Metals in Silicon* Substrates, in the Proceedings of the Symposium on *Diagnostic Techniques for Semiconductor Materials and Devices*, vol. 92–2, pp. 132–139. No Date.

ULTRA-LOW LEVEL STANDARD FOR CONCENTRATION MEASUREMENTS

BACKGROUND OF THE INVENTION

1. Field of the Invention

The present invention relates to materials, methods, and systems for calibrating concentration measurements, and more particularly to materials, methods, and systems for calibrating surface impurity concentration measurements for semiconductor fabrication.

2. Description of the Related Art

Modern semiconductor fabrication techniques, including those for Very Large Scale Integration (VLSI), require extraordinary levels of cleanliness. In fact, reduction of trace contaminant levels is a primary goal of semiconductor fabrication and research facilities. Performance and yield are both adversely affected by trace impurity levels. Today, ultra-clean fabrication and research facilities demand surface contamination levels below $10^{10}$ atoms/cm and future facilities will require levels below $10^9$ atoms/cm.

Consequently, the semiconductor industry, including researchers, wafer suppliers and device manufacturers, requires improved analytical techniques to measure organic and inorganic surface contaminants. Trace amounts of metallic contaminants are of particular concern and are known to seriously affect both performance and manufacturing yield of integrated circuits. To achieve the desired levels of cleanliness, extremely sensitive quantitative analysis techniques are required to measure impurity concentration levels. In turn, the equipment used in these techniques requires precise calibration. Examples of such quantitative analysis techniques include:

1. Total Reflection X-ray Fluorescence (TXRF), in which an X-ray beam strikes the surface to be examined at a grazing angle (below the "critical angle" or angle for total reflection) thus resulting in surface sensitivity of a few monolayers;
2. Time of Flight Secondary Ion Mass Spectroscopy (TOF-SIMS), in which surface impurity atoms are sputtered off by a pulsed ion beam and subsequently detected by a time of flight mass spectrometer; and
3. Heavy Ion Backscattering (HIBS), in which a high mass, moderate energy ion beam is backscattered by surface atoms, the characteristics of the backscattered ions depending on the species of the surface scatterer.

Calibration of each of these quantitative analysis techniques for low-level impurity concentrations has proved difficult.

In general, calibration of equipment used in quantitative analysis techniques is necessary because of the variety of factors that affect the measurement, such as background noise, variations in detector and collection efficiency, and variations in response from the impurity. Unfortunately, precise calibration of surface contamination measurement equipment typically requires the preparation of a tightly controlled reference standard with a precisely known impurity level. In this way, the actual response of the equipment can be calibrated against the known impurity level of a reference standard. Because it is difficult to precisely control the number of impurity atoms deposited on a reference standard, powerful analytical techniques have been used to characterize the reference standard before the reference standard can, itself, be used to calibrate other measurement equipment. For example, standards used for calibrating TXRF equipment have first been characterized by other methods, such as Atomic Absorption Spectrometry (AAS) or Inductively Coupled Plasma Mass Spectrometry ICP-MS. Unfortunately, many of these techniques suffer from their own calibration problems and from a similar lack of reference standards at concentration levels at or below $10^{10}$ atoms/cm$^2$. As a result, precise calibration standards for surface concentration measurements in the range now desired (i.e., at or below $10^{10}$ atoms/cm$^2$) are not generally available.

The problems inherent in many current calibration techniques can be illustrated in the context of TXRF, which is commonly used in the semiconductor industry to monitor the level of surface contamination on wafers at various stages of device fabrication. In order to provide a quantitative measurement of surface contamination levels, calibration curves have been measured based on controlled standard samples with known impurity concentration. However, current calibration techniques have proved unreliable at surface contamination levels on the order of $10^{10}$ atoms/cm$^2$. Round-robin measurements have been used with only marginal success in an attempt to mask inconsistencies among characterizations of reference standards. For example, round-robin test results reported to the ISO/TC 201/WG2 on Total X-ray Fluorescence Spectroscopy indicated inconsistencies in calibration data measured by a variety of different researchers despite the fact that they were using the same method. See e.g., *Third Working Draft, Surface chemical analysis—Determination of contamination elements contents on silicone wafer—Total reflections X-ray fluorescence spectroscopy (TXRF)*, ISO/TC 201/WG2 N 26, Nov. 28, 1995. Chief among the report's concerns were the accuracy of initial measurements of the impurity concentration and unintended contamination from external sources. These problems are compounded when contamination takes the form of the same impurity atom intentionally used in the standard, or when the originally known contamination levels decrease unpredictably. Annex C of the above report specifies compositions for, procedures for preparing, and methods for calibrating a TXRF measurement apparatus with a standard specimen.

SUMMARY OF THE INVENTION

It has been discovered that a concentration measurement device can be calibrated by performing a concentration measurement on a reference standard sample which includes a radioactive marker element. Because a count of decay products can be correlated with the number of atoms of the radioactive marker element, a precise count of decay products of the radioactive marker element is used to calculate an otherwise unknown number of atoms of the radioactive marker element on the reference standard sample. The calculated number of atoms of radioactive marker element is then used to calibrate a concentration measurement of the radioactive marker element by the concentration measurement device.

In one embodiment of the present invention, a reference standard sample includes an approximately 1 mm deposit of Pm-147 or Tc-99 as a radioactive marker element at a concentration level of approximately $10^{11}$ atoms/cm$^2$. In another embodiment of the present invention, a calibration system includes a radiation detector such as a beta, gamma, or X-ray counter/radiation detector whose efficiency is well known. In yet another embodiment of the present invention, a method for calibrating a concentration measurement includes depositing from stock solution, an approximately 1 mm spot of radioactive Pm-147 or Tc-99 on a Si wafer to form a reference standard sample, using a beta, gamma, or X-ray counter/radiation detector to determine the number of atoms of Pm-147 or Tc-99 on the Si wafer, and using a TXRF measurement of the reference standard sample to calibrate counts per second (cps) for Pm-147 or Tc-99 X-rays fluorescing under TXRF operating conditions to the number of atoms/cm$^2$ determined using the beta, gamma, or X-ray counter/radiation detector.

In still yet another embodiment of the present invention, a reference standard material for calibrating a concentration measurement apparatus includes a substrate and a radioactive marker element detectable by the concentration measurement apparatus. The radioactive marker element is on the substrate, has a known half-life, and is in an amount sufficient for reliable detection of radioactive decay products thereof.

In still yet another embodiment of the present invention, a method for calibrating a concentration measurement apparatus includes the steps of measuring a flux of radioactive decay products from a reference standard sample which includes a radioactive marker element having a known half-life, measuring a concentration of the radioactive marker element using the concentration measurement apparatus, and calculating a calibration adjustment using the known half-life of the radioactive marker element and the measured radioactive decay product flux.

In still yet another embodiment of the present invention, a method for characterizing a reference standard sample as a calibration standard for a concentration measurement apparatus includes the steps of measuring a flux of radioactive decay products of a radioactive marker element on the reference standard sample and calculating a concentration of the radioactive marker element using a known half-life of the radioactive marker element and the radioactive decay product flux measured in the flux measuring step.

In still yet another embodiment of the present invention, an apparatus includes a surface concentration measurement apparatus having a detector for generating a first signal indicative of a surface concentration measurement of a radioactive marker element on a reference standard sample and a calibration subsystem coupled to receive the first signal and to supply a calibration correction to the first signal using, in accordance with radioactive decay equations, a known half-life of the radioactive marker element and a measured radioactive decay product flux.

BRIEF DESCRIPTION OF THE DRAWINGS

The present invention may be better understood, and its numerous objects, features, and advantages made apparent to persons of ordinary skill in the art by referencing the accompanying drawings.

The use of the same reference symbols in different drawings indicates similar or identical items.

DETAILED DESCRIPTION OF THE PREFERRED EMBODIMENTS

Figure 1:
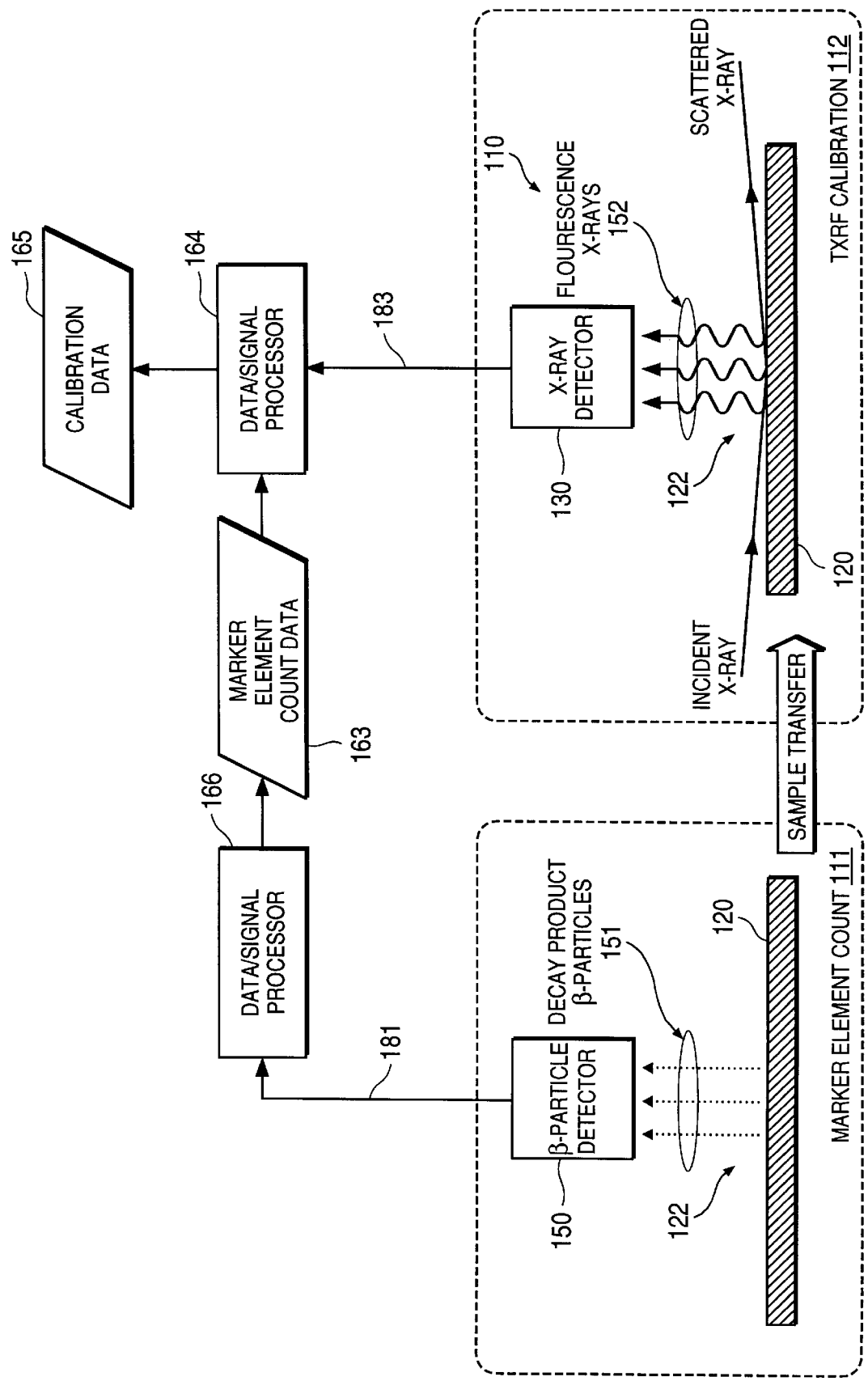
FIG. 1 depicts a system, apparatus, and method for calibrating a Total X-Ray Fluorescence (TXRF) apparatus for low-level surface concentration measurements using a reference standard sample in accordance with an exemplary embodiment of the present invention.

FIG. 1 depicts Total X-Ray Fluorescence (TXRF) equipment 110 for performing surface concentration measurements. TXRF equipment 110 is calibrated by performing a measurement (TXRF calibration 112) on a reference standard sample 120 which includes a radioactive marker element 122. Because radioactive marker element 122 decays at a known rate, i.e., because radioactive marker element 122 decays in accordance with a known half-life, $T_{1/2}$, a measurement (marker element count 111) of the flux of radioactive decay products from radioactive marker element 122 is indicative of the number of atoms of radioactive marker element 122 included on reference standard sample 120. Although this number decreases as radioactive marker element 122 decays, a measurement at a particular time is mathematically translatable to a corresponding number of radioactive marker element 122 atoms at any future (or past) time. A system, composition, or method in accordance with the present invention allows a number of atoms of radioactive marker element 122 so measured to be used for calibration of a surface concentration measurement apparatus which is sensitive to radioactive marker element 122.

In the TXRF embodiment of FIG. 1, the flux of X-rays received at X-ray detector 130 of TXRF equipment 110 from reference standard sample 120 (during TXRF calibration 112) is calibrated against the measured number of atoms of radioactive marker element 122. The result is calibration data 165 (e.g., fluorescence X-ray intensity corresponding to a particular concentration) which is then used for subsequent measurements by TXRF equipment 110. Variations on the reference standard sample configuration and on the analytic technique are described below.

In general TXRF equipment 110 operates as follows. When a specimen is irradiated with X-rays, fluorescence X-rays of energy characteristic of the elements that constitute the specimen are generated. The intensities of the fluorescence X-rays are proportional to the amounts of the corresponding elements. Geometric configurations which result in total reflection of the incident X-rays on the specimen reduce the intensity of the scattered X-rays and also help to localize the generation of fluorescence X-rays to near surface layers of the specimen. In this way, a spectrum of fluorescence X-ray with a large signal-to-background ratio can be obtained. Detection limits of such TXRF equipment depend on the atomic numbers and excitation energies of elements on the surface of the specimen and on photon flux and energy bandwidth of excitation X-rays, background noise, integration time, etc. Persons of ordinary skill in the art will recognize a wide variety of suitable TXRF configurations and operating parameters. See e.g., *Third Working Draft, Surface chemical analysis— Determination of contamination elements contents on silicone wafer—Total reflections X-ray fluorescence spectroscopy (TXRF)*, ISO/TC 201/WG2 N 26, Nov. 28, 1995 (specifying TXRF configurations and methods for surface concentration measurements on polished and epitaxial silicon wafer surfaces).

In an exemplary embodiment of the present invention, reference standard sample 120 includes an isotope of promethium (Pm-147) as radioactive marker element 122. Pm-147 has a half-life of approximately 2.5 years which is long enough to provide a useful reference standard lifetime, but short enough so that there are a sufficient number of decay products per second available for sampling from a small number of Pm-147 atoms. Furthermore, Pm-147 decays via beta decay, yielding relatively low energy β-particles (electrons) that require shielding with ordinary plastic, such as Lexan®, and are readily detectable using a beta counter.

Decay product counter 109 includes β-particle detector 150, which detects decay product β-particles 151 from the radioactive decay of Pm-147. A β-particle incidence signal 181 corresponding to the flux of decay product β-particles 151, typically in counts per second, is supplied from β-particle detector 150 to data/signal processor 166. Data/signal processor 166 in turn computes and supplies marker element count data 163, which, in the exemplary Pm-147 embodiment described above is Pm-147 count data. Suitable techniques for deriving a radioactive element count from a decay product incidence signal, such as β-particle incidence signal 181, are well known to persons of ordinary skill in the art. Data/signal processor 166 implements any such suitable techniques.

Given the solid angle subtended by β-particle detector 150, the efficiency of β-particle detector 150, and the number of decay product ε-particles per decaying atom of radioactive marker element 122, a measurement of the number of decay products emitted (i.e., β-particle incidence signal 181) yields the time rate of change for the number of radioactive marker element 122 atoms, or $dN(t)/dt$ where $N(t)$ is the number of undecayed atoms at a given time t.

In general, for atoms that decay directly to a stable isotope, the number of undecayed atoms is given by:

$$N(t) = N_0 e^{-Rt},$$

where $N_0$ is the number of undecayed atoms at t=0 (i.e., the approximate time at which the ratio measurement is made) and R is the decay rate which can be expressed in terms of the half-life $T_{1/2}$ as $R=\ln(2)/T_{1/2}$. Taking the time derivative of the decay equation and solving for $N_0$ one finds that:

$$N_0 = \frac{-e^{Rt}}{R} \frac{dN(t)}{dt}.$$

Thus, with the derivation of $dN(t)/dt$ from β-particle incidence signal 181, and with a known half-life, $T_{1/2}$, for the radioactive marker element 122 (approximately 2.5 years for Pm-147), it is possible to determine the number of radioactive marker element atoms 122 present on reference standard sample 120. In the exemplary embodiment of FIG. 1, data/signal processor 166 performs such a determination and results thereof are represented as marker element count data 163. Typically, marker element count 111 and TXRF calibration 112 will be performed at close to the same time, such that $N_{t=marker\_count} \approx N_{t=TXRF\_calibration}$. Alternatively, a previously determined radioactive marker element 122 count can be updated in accordance with the above decay equations if the concentration measurement is performed after marker element count 111. In the case of non-destructive concentration measurement techniques, such as TXRF, a marker element count 111 may even be performed after the concentration measurement to be calibrated. Persons of ordinary skill in the art will appreciate suitable temporal corrections to radioactive marker element 122 counts in accordance with the above decay equations.

In TXRF calibration 112 mode, the flux of fluorescence X-rays 152 detected from atoms of radioactive marker element 122 on reference standard sample 120 by X-ray detector 130 (signal 183) is calibrated to the count (or concentration) of radioactive marker element 122 calculated as described above. For example, a TXRF scan of reference standard sample 120 might yield 100 counts per second per square centimeter (cps/cm$^2$) when scanning for Pm-147 atoms. If, as described above, reference standard sample 120 is determined to include $10^{10}$ radioactive marker element 122 atoms/cm$^2$, a subsequent scan for Pm-147 on an unknown sample that yields 50 cps/cm$^2$ corresponds to a concentration of 5×10$^9$ atoms/cm$^2$. Calibration methods, including methods for extrapolating a calibration for a particular element, e.g., radioactive marker element 122, to other elements of interest are well known in the art. For example, relative sensitivity factors allow a calibration for a particular element (typically Fe or Ni) to be parlayed into calibrations for other elements of interest. Methods for determining such relative sensitivity factors are well known to persons of ordinary skill in the art. See e.g., *ANNEXB, Third Working Draft, Surface chemical analysis—Determination of contamination elements contents on silicone wafer—Total reflections X-ray fluorescence spectroscopy (TXRF)*, ISO/TC 201/WG2 N 26, Nov. 28, 1995. Data/signal processor 164 implements any such suitable calibration methods.

FIG. 1 includes an exemplary decomposition of computations for processing raw signals from TXRF equipment 110 to produce calibration data 165 for use in low-level concentration measurements. Persons of ordinary skill in the art will recognized a large variety of suitable alternative decompositions of calibration computations. For example, much of the signal processing may be provided by hardware or software provided as part of a data acquisition and control interface to measurement equipment. Additionally, computations to arrive at calibration data do not necessarily require a physically connected system. Therefore, computations for determining calibration data 165 may be completed manually and raw count per second measurements from TXRF equipment 110 may be adjusted manually in accordance with the calibration data 165. Similarly, the functionality of data/signal processor 166 and data/signal processor 164, together with an intermediate representation of marker element count data 163, may be combined to implement a calibration subsystem in hardware and or software.

Although one presently preferred embodiment of reference standard sample 120 includes Pm-147 as radioactive marker element 122, alternative radioactive marker element choices are also suitable. In general, radioactive marker element 122 should be detectable by the concentration measurement technique (e.g., TXRF, TOFSIMS, etc.) being calibrated and should be chosen based on factors including:

1. radioactive decay into relatively low energy decay products so as not to pose a threat to personnel or processing equipment and not to require additional shielding;
2. radioactive decay into decay products that are easy to detect by either the concentration measurement apparatus itself or alternate readily available equipment; and
3. a radioactive decay rate sufficiently low to ensure reference standard longevity yet sufficiently high to insure an adequate count rate for determining the number of radioactive atoms present on the reference standard.

A presently-preferred embodiment including Pm-147 as radioactive marker element 122 has several advantages. First, there are no naturally occurring isotopes of Pm. As a result, unlike radioactive isotopes of Fe, Cr, etc., there is little risk that the number of Pm-147 atoms on reference standard sample 120 will be affected by sources of contamination within a semiconductor fabrication or research facility. Second, Pm-147 has a half-life of approximately 2.5 years which is long enough to provide a useful reference standard lifetime, but short enough so that there are sufficient decay events per second from a small number of atoms to provide a well-behaved, easily-measured flux of decay products. Given such a half-life, a reference standard sample 120 based on as little as $10^8$ Pm-147 atoms is practical. Additionally, Pm-147 produces β-particles as decay products that require no additional shielding for personnel safety and are readily detectable using beta detector such as a proportional counter.

In general, a search set for suitable radioactive marker element 122 instances is defined by the set of elements detectable by a measurement device to be calibrated and by the set of isotopes for which detectable decay products exist. An element near the middle of a measurement device detection window is desirable, though not essential. For a typical TXRF apparatus, the detection window includes elements of atomic number greater than 14 (i.e., Si). For high Z elements such as Pm and Tc, a TXRF apparatus would typically use L-lines or M-lines, rather than K-lines typical for lower Z elements. For typical TOF-SIMS and HIBS apparati, the detection window includes all elements in the periodic table.

In one alternative embodiment, radioactive marker element 122 is Tc-99. Tc-99, like Pm-147, is a radioactive isotope of a non-naturally occurring element. Also, like Pm-147, Tc-99 decays producing β-particles. Unfortunately, since the half-life of Tc-99 is $2.12 \times 10^5$ years, decay events are infrequent and a significant amount of Tc-99 is necessary to produce an adequate flux of decay products for reliable determination of radioactive marker element 122 count. A Tc-99 concentration on the order of $10^{13}$ to $10^{14}$ atoms/cm$^2$ is preferred for adequate radioactivity measurement.

In the context of a radioactive marker element 122 which decays producing β-particles, a half-life in the range of a few weeks to a few years is preferable. A half-life in the range of 1 to 5 is more preferable and a half-life in the range of 2 to 3 is most preferable. Desirable half-life ranges are similar for a radioactive marker element 122 which decays producing X-rays.

Other alternative embodiments include naturally occurring radioactive marker elements having relatively low energy decay products and a radioactive decay rate sufficiently low to ensure reference standard longevity yet sufficiently high to insure an adequate count rate for determining the number of radioactive atoms present on the reference standard. For example, Fe-55, Cr-51, and Mn-54, Ca-45, V-49, Sc-46 are also suitable. Although a reference standard sample 120 based on such alternative radioactive marker elements is more susceptible to contamination than one based on a radioactive marker element 122 not occurring in nature, radioactive isotopes of naturally occurring elements are also suitable. In the case of concentration measurement techniques which resolve individual isotopes (e.g., TOF-SIMS), a nonnaturally occurring radioisotope of an element which otherwise occurs in nature is less susceptible to contamination. Several suitable naturally occurring radioactive marker elements are described in the context of a ratio-based reference standard described in a co-pending patent application entitled, "Absolute Standard Reference Materials for Low-Level Concentration Measurements," Ser. No. 08/712,716 naming Hossain as inventor and filed on even date herewith, the entirety of which is hereby incorporated by reference.

Whatever the element and isotope selected as radioactive marker element 122, a small amount of radioactive marker element 122 is deposited on the surface of a clean substrate typical of those used for concentration measurements, e.g., in the case of a TXRF measurement, a <100> oriented silicon wafer. Deposition can be accomplished by a variety of techniques including spin-coating, wafer immersion, and vapor-phase deposition. In one embodiment, a microdroplet of the reference standard material is deposited onto the center of a silicon wafer and then dried under controlled environmental conditions.

Figure 2:
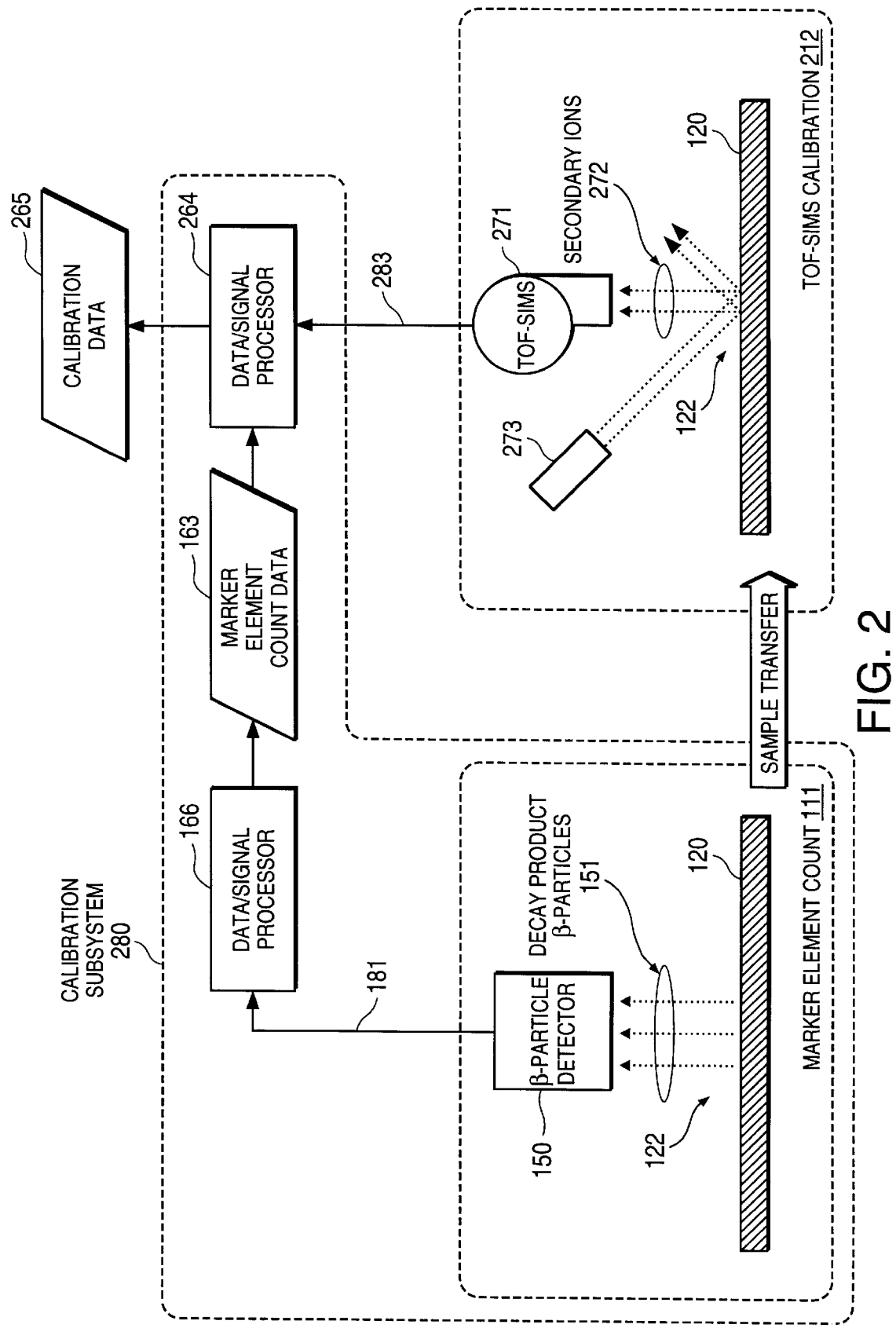
FIG. 2 depicts a system, apparatus, and method for calibrating a Time Of Flight-Secondary Ion Mass Spectroscopy (TOF-SIMS) apparatus for low-level surface concentration measurements using a reference standard sample in accordance with an exemplary embodiment of the present invention.

FIG. 2 depicts an alternative Time Of Flight-Secondary Ion Mass Spectroscopy (TOF-SIMS) embodiment in which TOF-SIMS 271 (rather than a TXRF measurement apparatus) is calibrated for low-level concentration measurements in accordance with the present invention. As before, a β-particle detector 150 detects decay product β-particles 151 from radioactive marker element 122 on reference standard sample 120. β-particle incidence signal 181 is processed by data/signal processor 166 to provide marker element count data 163. Reference standard sample 120 is transferred to TOF-SIMS 271 for measurement and for the actual calibration. In the embodiment of FIG. 2, signal 283 includes a calibration measurement of radioactive marker element 122 concentration based on secondary ions 272 measured by TOF-SIMS 271. Decay product detection at marker element counter 111 and calibration measurements at TOF-SIMS 271 are typically performed in sequence at approximately the same time so that intertemporal decay of radioactive marker element 122 is insignificant. Alternatively, the mathematical manipulations associated with either data/signal processor 166 or data/signal processor 264 can be modified to accurately represent the time lag between decay product measurement and ratio measurement. Suitable modifications based on the decay equations described above will be apparent to persons of ordinary skill in the art.

Decay product β-particles 151 are detected by a β-particle detector 150, illustratively a proportional counter. However, a variety of suitable alternative embodiments for marker element counter 111 will be appreciated by persons of ordinary skill in the art. In particular, in one such suitable alternative embodiment, the decay product β-particle measurement is performed using a well characterized β-particle detector at a research laboratory such as the National Institute of Standards and Technology, NIST, and supplied as radioactive marker element 122 count (or concentration) at a particular time. TOF-SIMS 271 is then calibrated as described above using the supplied radioactive marker element 122 count as marker element count data 163.

Figure 3:
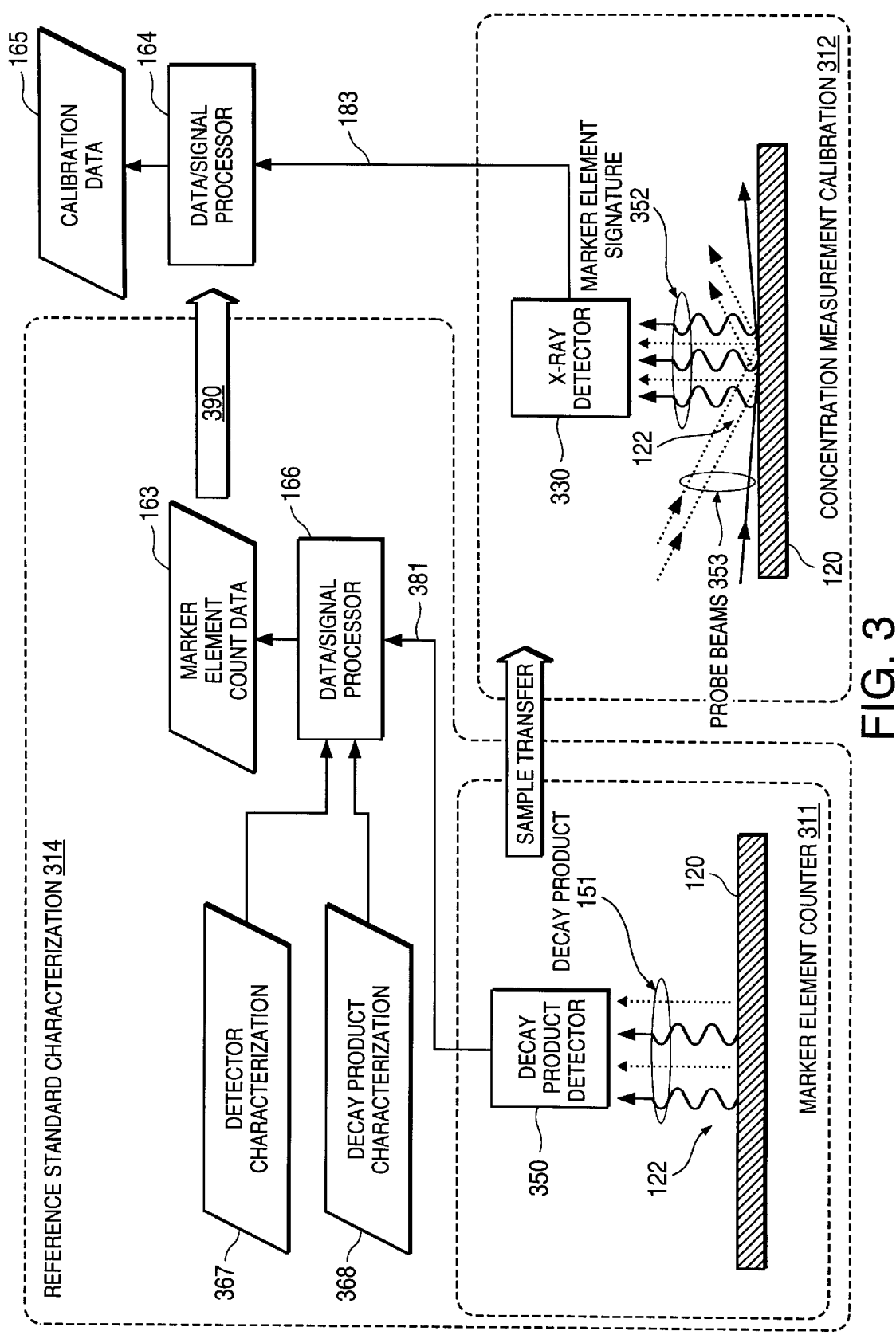
FIG. 3 depicts a system, apparatus, and method for characterizing the concentration of a radioactive marker element on a reference standard sample and for providing the reference standard sample so characterized for calibration of a concentration measurement apparatus in accordance with an exemplary embodiment of the present invention.

FIG. 3 depicts yet another alternative embodiment in which reference standard sample 120 is characterized and supplied with characterization data 390, including marker element count (or concentration) data. Reference standard characterization 314 is performed independent of detector calibration 312 and may be performed off-site. In the embodiment of FIG. 3, detector 330 detects radioactive marker element 122 signature 352 which is generated under excitation from probe beams 353. Detector 330 is representative of detectors for a wide variety of concentration measurement techniques, including TXRF, TOF-SIMS, XRF, SIMS, AES, etc. Probe beams 353 are representative of a variety excitation technique corresponding to these concentration measurement techniques.

As before, the embodiment of FIG. 3 builds on a measurement of decay products from radioactive marker element 122. Marker element counter 311 includes a decay product detector 350, which in various alternative embodiments detects β-particles, X-rays, γ-rays, α-particles, etc. In a presently preferred embodiment, radioactive marker element 122 decays, emitting β-particles, and decay product detector 350 is therefore a β-particle detector, although decay products of varying energies, masses, and other characteristics are also possible. Suitable detector designs and shielding requirements will be appreciated by persons of ordinary skill in the art.

Reference standard characterization 314 is potentially performed off-site of the eventual detector calibration 312. In one such embodiment, characterization data 390 is computed from its precursor, β-particle incidence signal 381. Reference standard sample 120 is then supplied (e.g., by a vendor of characterized reference samples) with characterization data 390 for use in the calibration of any suitable detector 330 (e.g., X-ray detector 130, TOF-SIMS 271, etc.). In such an embodiment, characterization data 390 includes both radioactive marker element 122 count data and an indication of the time at which the count data is baselined.

The particular marker element counter 311 configuration depends on the type of radioactive decay product emitted by the radioactive marker element 122. In the case of Pm-147 which emits β-particles, a presently preferred radioactive decay product measuring technique is to use a proportional counter. For a radioactive marker element 122 which emits X-rays, an attractive radioactive decay product measuring technique is to use the X-ray detector built into a TXRF apparatus. In the case of a TXRF measurement calibration, this avoids the use of a second apparatus, and allows the calibration measurement and the radioactive element measurement to be made in rapid succession without removing the reference standard. In such an embodiment, a measurement of decay product X-ray flux is performed while the TXRF incident X-ray source is turned off or otherwise prevented from irradiating reference standard sample 120. The TXRF incident X-ray source is then turned on or otherwise made to irradiating reference standard sample 120 for TXRF calibration 112. For alternative embodiments in which radioactive marker element 122 decays producing decay products other than β-particles and X-rays, marker element counter 311 includes a corresponding decay product detector.

While the invention has been described with reference to various embodiments, it will be understood that these embodiments are illustrative and that the scope of the invention is not limited to them. Many variations, modifications, additions, and improvements of the embodiments described are possible. For example, a broad range of selections for radioactive marker element 122 is possible. In addition, radioactive marker elements having non-β-particle decay products are possible with corresponding modifications to a marker element counter. A wide variety of measurement techniques are possible for counting decay products of radioactive marker element 122. With respect to system and method embodiments, data/signal processing configurations described herein are merely illustrative. Alternative embodiments of systems and methods for calibrating a concentration measurement device may incorporate manual or automated processes or a combination of manual and automated processes. Particular descriptions of computations and intermediate data are similarly illustrative. Alternate configurations and implementations of the underlying computations are also possible. Additionally, a wide variety of concentration measurement techniques may be calibrated using systems, compositions, and methods in accordance with the present invention. These and other variations, modifications, additions, and improvements may fall within the scope of the invention as defined in the claims which follow.

What is claimed is:

1. A reference standard material for calibrating a concentration measurement apparatus, the reference standard material comprising:
   a substrate; and
   a radioactive marker element detectable by the concentration measurement apparatus for calibration thereof, the radioactive marker element being on the substrate, having a known half-life, and in an amount sufficient for reliable detection of radioactive decay products thereof.

2. A reference standard material, as recited in claim 1, wherein a flux of decay products of the radioactive marker element provides a precise indication of a number of atoms of the radioactive marker element on the substrate.

3. A reference standard material, as recited in claim 1, wherein the radioactive marker element is a non-naturally occurring element.

4. A reference standard material, as recited in claim 1, wherein the radioactive marker element is Pm-147.

5. A reference standard material, as recited in claim 1, wherein the radioactive marker element is Tc-99.

6. A reference standard material, as recited in claim 1, wherein the radioactive marker element is a naturally occurring element.

7. A reference standard material, as recited in claim 1, wherein the radioactive marker element is Fe-55.

8. A reference standard material, as recited in claim 1, wherein the radioactive decay products are substantially limited to radioactive decay products of a type and flux for which for which shielding is substantially unnecessary for personnel safety.

9. A reference standard material, as recited in claim 1, wherein the radioactive decay products are substantially limited to β-particles.

10. A reference standard material, as recited in claim 1, wherein the radioactive decay products are substantially limited to X-rays.

11. A reference standard material, as recited in claim 1, wherein the half-life of the radioactive marker element and amount thereof are such that a flux of decay products impinging on a detector therefor is reliably measurable to a precision of one part in one hundred.

12. A reference standard material, as recited in claim 1, wherein decay products of the radioactive marker element include β-particles; and
   wherein the radioactive marker element has a half-life longer than a week and shorter than ten years.

13. A reference standard material, as recited in claim 1, wherein decay products of the radioactive marker element include β-particles; and
   wherein the radioactive marker element has a half-life longer than one year and shorter than five years.

14. A reference standard material, as recited in claim 1, wherein decay products of the radioactive marker element include β-particles; and
   wherein the radioactive marker element has a half-life longer than two years and shorter than three years.

15. A reference standard material, as recited in claim 1, supplied in association with a calculated concentration of t he radioactive marker element and an indication of a time at which the concentration of the radioactive marker element is baselined.

16. A method for calibrating a concentration measurement apparatus, the method comprising the steps of:
   providing a reference standard sample including a radioactive marker element having a known half-life;

measuring a flux of radioactive decay products from the reference standard sample;

measuring a concentration of the radioactive marker element using the concentration measurement apparatus; and calculating a calibration adjustment to the concentration measured in the concentration measuring step using the known half-life of the radioactive marker element and the radioactive decay product flux measured in the flux measuring step.

17. A method, as recited in claim 16, wherein the concentration measuring step is performed using Total X-Ray Fluorescence (TXRF) and the concentration measurement apparatus so calibrated is a TXRF apparatus.

18. A method, as recited in claim 16, wherein the concentration measuring step is performed using Time of Flight-Secondary Ion Mass Spectroscopy (TOFSIMS) and the concentration measurement apparatus so calibrated is a TOF-SIMS apparatus.

19. A method, as recited in claim 16, wherein the concentration measuring step is performed using Heavy Ion Backscattering (HIBS) and the concentration measurement apparatus so calibrated is a HIBS apparatus.

20. A method, as recited in claim 16,
wherein the radioactive decay products of the radioactive marker element are substantially limited to β-particles; and wherein the radioactive decay product measuring step is performed using β-particle detector.

21. A method, as recited in claim 16,
wherein the concentration measuring step is performed using Total X-Ray Fluorescence (TXRF) and the concentration measurement apparatus so calibrated is a TXRF apparatus;

wherein the radioactive decay products of the radioactive marker element are substantially limited to X-rays; and wherein the radioactive decay product measuring step is performed using an X-ray detector of the TXRF apparatus in passive mode.

22. A method, as recited in claim 16, wherein the calibration adjustment calculating step includes the steps of:

calculating, in accordance with radioactive decay equations, the concentration of the radioactive marker element using the known half-life of the radioactive marker element, the measured radioactive decay product flux, and time elapsed between the radioactive decay product flux measurement and the concentration measurement; and calculating an adjustment factor for future concentration measurements based on a discrepancy between the concentration calculated in accordance with the radioactive decay equations and that measured using the concentration measurement apparatus.

23. A method, as recited in claim 22, wherein the radioactive decay product flux measurement is performed before the concentration measurement.

24. A method, as recited in claim 22, wherein the radioactive decay product flux measurement is performed after the concentration measurement.

25. A method, as recited in claim 22, wherein the radioactive decay product flux measurement is performed at approximately the same time as the concentration measurement.

26. An apparatus comprising:

a surface concentration measurement apparatus having a detector for generating a first signal indicative of a surface concentration measurement of an amount of a radioactive marker element on a reference standard sample; and a calibration subsystem coupled to receive the first signal and to supply a calibration correction to the first signal using, in accordance with radioactive decay equations, a known half-life of the radioactive marker element and a measured radioactive decay product flux.

27. An apparatus, as recited in claim 26, wherein the calibration subsystem includes:

a decay product detector for generating a second signal indicative of the radioactive decay product flux from the radioactive marker element on the reference standard sample; and a processor coupled to receive the second signal from the decay product detector, the processor configured to calculate the calibration correction based on a discrepancy between a radioactive marker element surface concentration calculated in accordance with the radioactive decay equations and the known half-life and that indicated by the first signal.

28. An apparatus, as recited in claim 26, further comprising:

storage coupled to receive the calibration correction from the calibration subsystem and coupled to supply the calibration correction for correction of a second signal from the detector, the second signal indicative of a surface concentration measurement of a non-reference sample.

29. An apparatus, as recited in claim 27, wherein the decay product detector includes a β-particle detector.

30. An apparatus, as recited in claim 27, wherein the decay product detector includes an X-ray detector.

31. An apparatus, as recited in claim 26, wherein the surface concentration measurement apparatus includes a Total X-Ray Fluorescence (TXRF) apparatus.

32. An apparatus, as recited in claim 26, wherein the surface concentration measurement apparatus includes a Time Of Flight Secondary Ion Mass Spectrometer (TOF-SIMS) apparatus.

33. An apparatus, as recited in claim 26, wherein the radioactive decay products of the radioactive marker element are substantially limited to β-particles, the measured radioactive decay product flux being an β-particle measurement.

34. An apparatus, as recited in claim 27,
wherein the surface concentration measurement apparatus includes a Total X-Ray Fluorescence (TXRF) apparatus having an X-ray detector for detecting fluorescence X-rays in a surface concentration measurement mode;

wherein the radioactive decay products of the radioactive marker element are substantially limited to X-rays; and wherein the decay product detector is an X-ray detector of the TXRF apparatus operating in a passive measurement mode.

* * * * *